United States Patent [19]

Seedhom et al.

[11] Patent Number: 5,209,756
[45] Date of Patent: May 11, 1993

[54] LIGAMENT FIXATION STAPLE

[75] Inventors: Bahaa B. Seedhom, Roundabout Farm, Padside, Thornthwaite, Harrogate, HG3 4AL; Simon Collins, Mapplewell; Anthony C. Swann, Chapeltown, all of England

[73] Assignee: Bahaa Botros Seedhom, Leeds, United Kingdom

[21] Appl. No.: 720,833

[22] PCT Filed: Nov. 5, 1990

[86] PCT No.: PCT/GB90/01694
§ 371 Date: Jul. 10, 1991
§ 102(e) Date: Jul. 10, 1991

[87] PCT Pub. No.: WO91/06249
PCT Pub. Date: May 16, 1991

[30] Foreign Application Priority Data

Nov. 3, 1989 [GB] United Kingdom ............... 8924806

[51] Int. Cl.⁵ ............................................. A61B 17/00
[52] U.S. Cl. ..................................... 606/151; 606/219; 606/220; 606/75; 606/53; 623/13
[58] Field of Search ............... 606/151, 219, 220, 221, 606/60, 75, 72, 99; 623/13

[56] References Cited

U.S. PATENT DOCUMENTS 3,973,277 8/1976 Semple et al. ................... 623/13
4,278,091 7/1981 Borzone ......................... 606/219 X
4,728,329 3/1988 Mansat ............................ 623/13

FOREIGN PATENT DOCUMENTS

0467484 8/1950 Canada ............................ 606/75

Primary Examiner—Stephen C. Pellegrino
Assistant Examiner—Jeffrey A. Schmidt
Attorney, Agent, or Firm—Workman, Nydegger & Jensen

[57] ABSTRACT

A fixation device for securing a prosthetic ligament to a bone and which comprises a bone staple having a head portion by means of which the staple can be driven into the bone, and a pair of legs extending from the head and having ends engageable into the bone, characterized by a stirrup for guiding the driving movement of the staple and arranged also to cooperate with the staple in order to enable the prosthetic ligament to engage the staple and the stirrup and to be securable to the bone upon completion of driving of the staple into the bone, the stirrup comprising two generally parallel side portions which define guides to receive the legs of the staple and to guide the driving movement of the legs, and also defining an aperture through which the ligament can be taken prior to securement of the ligament to the bone.

17 Claims, 7 Drawing Sheets

LIGAMENT FIXATION STAPLE

This invention relates to a fixing device for securing a ligament to a bone by use of a bone staple. Bone staples are employed for attachment of artificial ligaments to bones during implantation to secure the ligament while tissue ingrowth occurs.

This invention also relates to a tool for use in implantation of a fixation device which includes a bone staple, and to a ligament adapted for use with the staple.

Conventional bone staples used for fixing ligaments to bones are generally U shaped, the ligament being trapped between the head of the staple and the bone when the staple is driven home. Unfortunately, simple staples become loose quickly, and the ligament slips thus becoming ineffective.

According to one aspect of the present invention there is provided a fixation device for securing a ligament to a bone and which comprises a bone staple having a head portion by means of which the staple can be driven into the bone, and a pair of legs extending from the head and having ends engageable into the bone, characterised by a stirrup for guiding the driving movement of the staple and arranged also to co-operate with the staple in order to enable the ligament to engage with the staple and the stirrup and to be securable to the bone upon completion of driving of the staple into the bone, said stirrup having guides to receive the legs of the staple and to guide the driving movement of the legs, and also defining an aperture through which the ligament can be taken prior to securement of the ligament to the bone.

During the implantation of the staple, a ligament is threaded through the aperture around the stirrup and the stirrup is located upon the staple legs with the ligament under the desired degree of tension. The staple is then driven into the bone to anchor the ligament.

The invention is particularly suitable for use in securing a prosthetic ligament to a bone. However, it should be understood that the fixing device of the invention may be used to secure ligaments of, or derived from natural material of a patient, or a donor, and including natural ligamentous tissue, autogenous tissue and allograft tissue. Therefore, for the purposes of this specification, all such materials i.e. natural or prosthetic, are intended to be included by the term "ligament".

In a first preferred embodiment of the invention, cross members extend between the side portions at locations between the aperture and guide positions through which the staple legs are received. The staple legs are prevented by the cross members from contacting and possibly damaging the ligament. In addition insertion of the legs through the stirrup is not impeded by the ligament. Less material is necessary for the staple to have a desired mechanical strength than if the cross members were outside the staple legs.

In an alternative embodiment of the invention, the cross members are disposed outwardly of the positions through which the staple legs are received. The ligament and staple legs may either by received in respective apertures in the stirrup, or may be received in a common elongate aperture.

The stirrup is preferably symmetrical in that the top and bottom surfaces are identical, avoiding the possibility that the stirrup may be installed upside down. In addition the stirrup may be inverted after the ligament has been threaded through it, wrapping the ligament around the stirrup to afford more secure attachment after implantation.

The stirrup may incorporate chamfered or otherwise profiled edges to minimise wear of the ligament. Spikes may be provided to the underside of the stirrup to secure the latter to ligament or adjacent bone.

The side portions of the stirrup adjacent the ligament receiving aperture may be provided with raised portions or slots to define a guideway for the ligament, straining the latter against lateral movement.

Use of the bone staple in accordance with this invention confers a number of advantages. Implantation is simple and does not require specialist tools. Only a single staple is required at each end of the ligament and the resultant assembly is unobtrusive having a small, low profile. Fatigue resistance and tensile strength are superior to those of other currently practiced techniques.

The invention is further described by means of example but not in any limitative sense, with reference to the accompanying drawings of which:

FIGS. 13 to 15 illustrate a tool for implantation of a bone staple; and.

Figure 1:
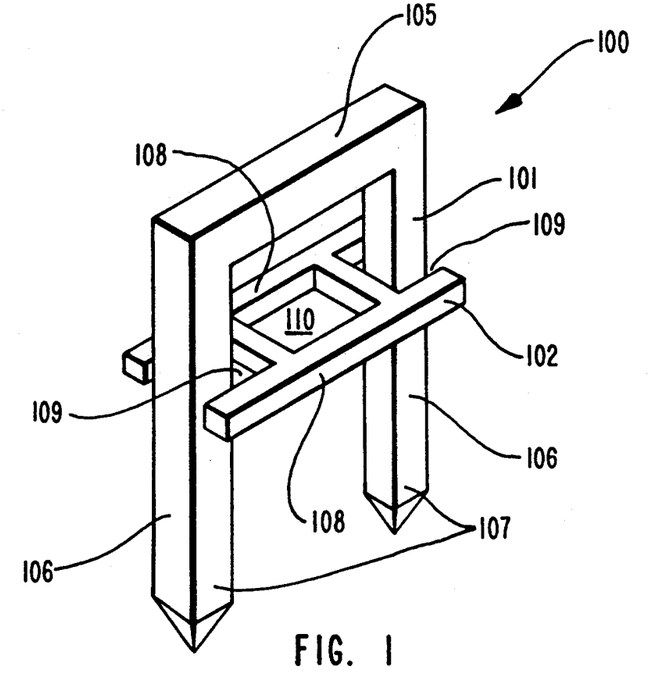
FIG. 1 is a perspective illustration of a first embodiment of fixation device according to the invention.
Figure 2:
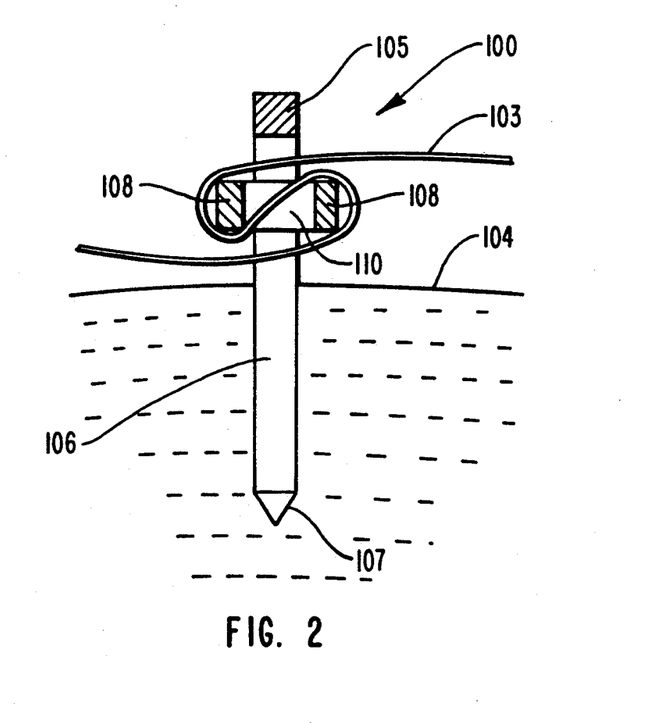
FIG. 2 shows the mode of use of the first embodiment in order to anchor a prosthetic ligament to a bone.

Referring first to FIGS. 1 and 2 of the drawings, a fixation device according to the invention is designated generally by reference 100, and comprises a U-shaped bone staple 101 and a co-operating stirrup 102. The device is intended to secure a prosthetic ligament 103 to a suitable site in a bone 104, and the staple 101 has a head portion 105, which forms the base of the U-shaped staple, and by means of which the staple 101 can be driven into the bone 104.

The staple 101 also has a pair of legs 106 extending away from the head portion 105, and having sharpened ends 107 which are engageable into the bone 104.

The stirrup 102 serves to guide the driving movement of the staple 101 and is arranged also to co-operate with the staple 101 in order to enable the prosthetic ligament 103 to engage with the staple 101 and the stirrup 102 in such a way that the ligament 103 can be secured to the bone 104 upon completion of driving of the staple 101 into the bone 104.

The stirrup 102 comprises two generally parallel side portions 108 which are laterally spaced apart from each other and which define guides 109 which receive the legs 106 of the staple 101, and also guide the driving movement of the legs.

In addition, the shape of the stirrup 102 is such that it defines an aperture 110 through which the ligament 103 can be taken or "threaded", as shown in FIG. 2, prior to securement of the ligament 103 to the bone 104.

FIGS. 1 and 2 show a first embodiment of fixation device according to the invention, and in which the bone staple 101 can take the form of any known constructions of this type suitable for this use. The stirrup 102 which is shown in FIGS. 1 and 2 comprises a first embodiment, and which is shown in more detail on its own in FIG. 3 of the drawings. In this construction of the stirrup 102, the guides 109 are defined at the ends of the stirrup, and take the form of recesses defined by end regions 111 of the side portions 108, and by cross pieces 112 which extend perpendicularly between and interconnect the side members 108. The cross members 112 also define a central recess which forms the aperture 110 through which the ligament 103 is taken. However, it should be understood that the stirrup construction shown in FIGS. 1 to 3 represent just one example of an arrangement in which a bone staple can co-operate with a stirrup in such a way that a ligament can be reliably secured to the assembly of staple and stirrup after the staple has been driven into the bone.

The ligament 103 preferably comprises a woven or other suitable form of artificial or prosthetic ligament, and the aperture 110 is of such a size that it can receive the ligament to pass therethrough, whereas the cross members 112 prevent the ligament from being damaged by the legs 106 of the staple 101 during insertion of the staple legs, and also provides a lightweight rugged structure.

Figure 3:
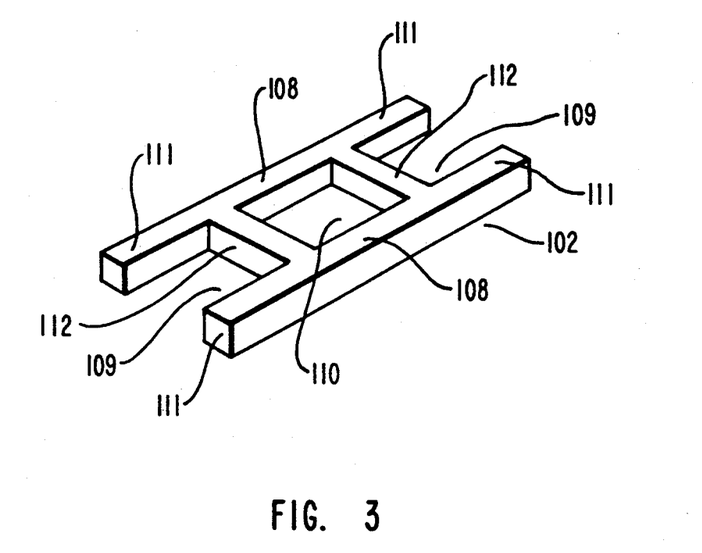
FIG. 3 is a perspective illustration and showing in more detail a stirrup of the fixation device shown in FIGS. 1 and 2.

The construction of staple 102 shown in FIGS. 1 to 3 comprises one construction which may be used in a fixation device according to the invention, but further constructions of stirrup are shown in FIGS. 4 to 12.

Figure 4:
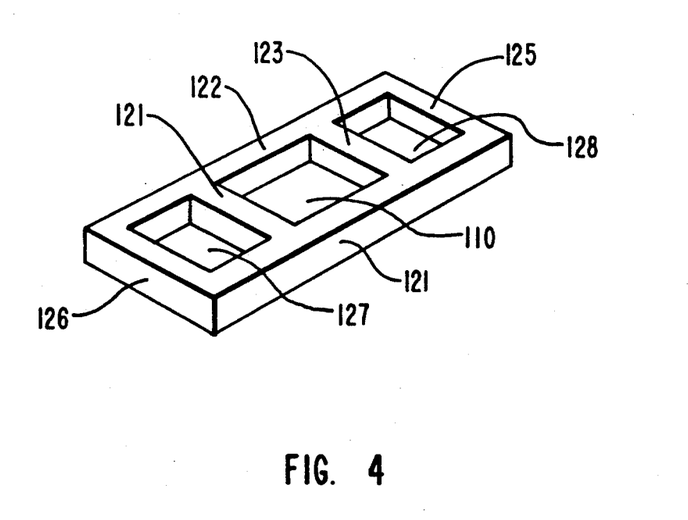
FIGS. 4 to 12 each show in perspective illustration further constructions of stirrup which may be used with a bone staple to form further embodiments of fixation device according to the invention.

FIG. 4 illustrates an alternative embodiment of the invention wherein the side portions 121, 122 are connected by first cross members 123, 124 and are further connected by cross members 125, 126 so that the staple receiving apertures 127, 128 are enclosed. However, the embodiment shown in FIG. 3 has the advantage over that shown in FIG. 4 in that the staple may be inserted at an angle, that is without being perpendicular to the stirrup. This facilitates surgical implantation.

Figure 5:
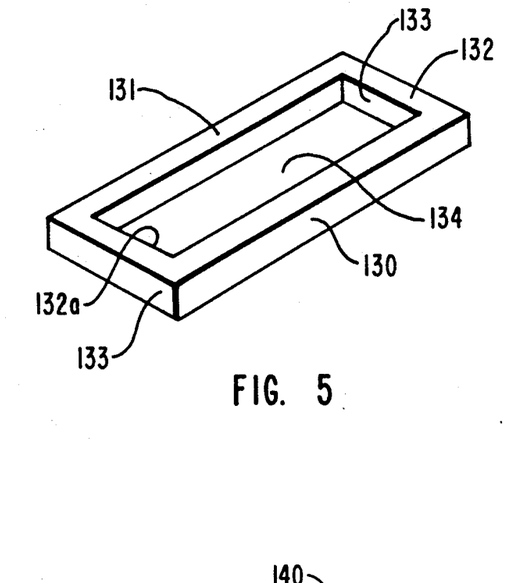
Figure 5A:
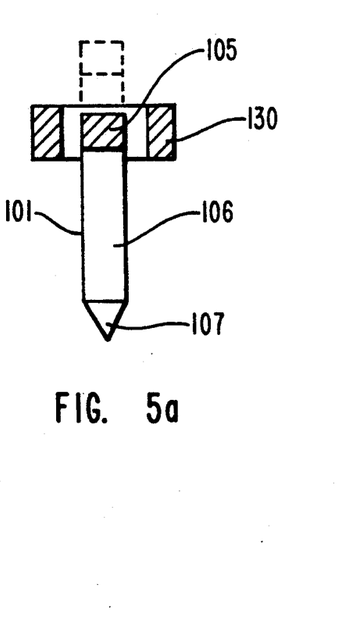

FIG. 5 illustrates a simple but very effective embodiment of the invention wherein side portions 130, 131 are supported by cross members 132, 133 located at the ends of the side portions to define a single aperture 134 to receive the staple legs and the ligament. The legs of the staple are guided by engagement with the inside faces 132a, 133a of the cross members 132, 133 (which act as guides), and as the staple is driven into the bone, the head of the staple can be located substantially within the plane of the stirrup, as shown in FIG. 5a. The ligament is omitted from FIG. 5a for clarity, but will be wound around the stirrup in similar manner to that which is shown in FIG. 2, and will be held in position very reliably by this arrangement.

Figure 6:
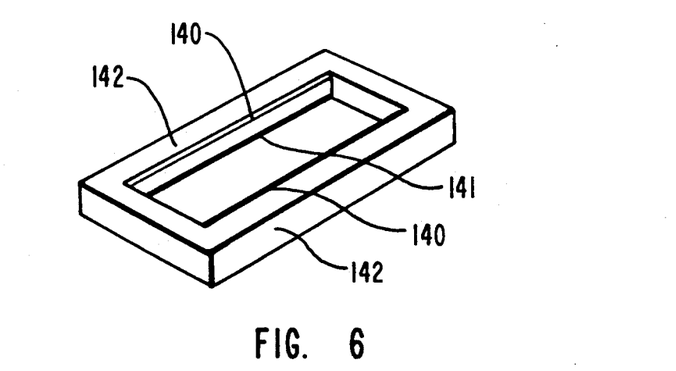

FIG. 6 illustrates a further embodiment similar to that shown in FIG. 5 with the inclusion of chamfered edges 140, 141 on the side portion 142 to prevent damage to the ligament by passage across the sharp corners of the side portions 142.

Figure 7:
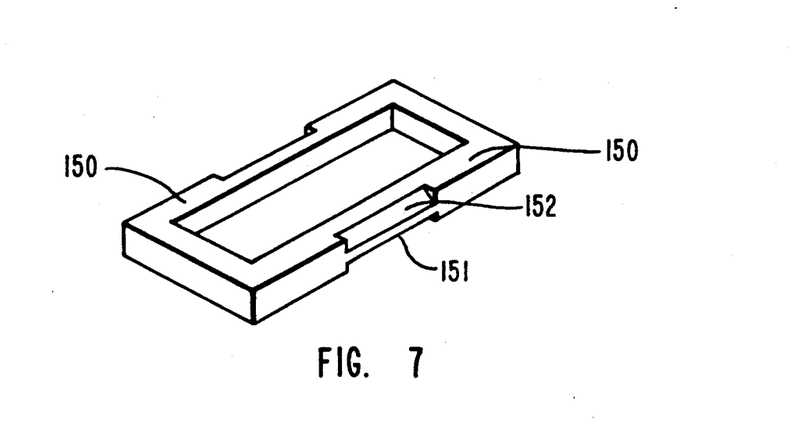

FIG. 7 illustrates a further embodiment wherein the outer edges of the side portions 150 have recessed portions 151, 152 to minimise damage to the ligament and also to provide a guide restraining lateral motion of the latter to facilitate implantation.

Figure 8:
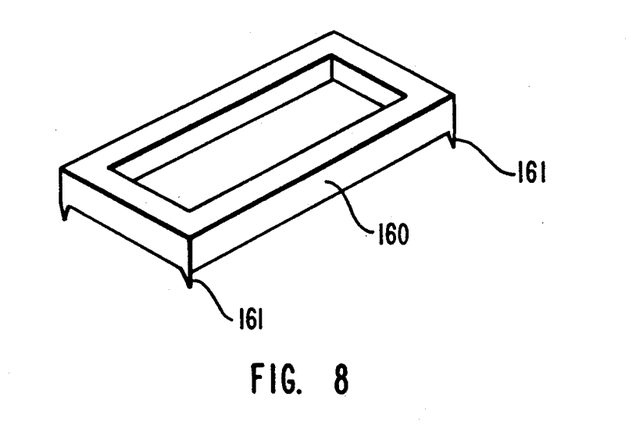

FIG. 8 shows a further embodiment of the invention wherein the ends of the side portions 160 carry spikes 161 which serve to engage the stirrup against the surface of the bone during implantation.

Figure 9:
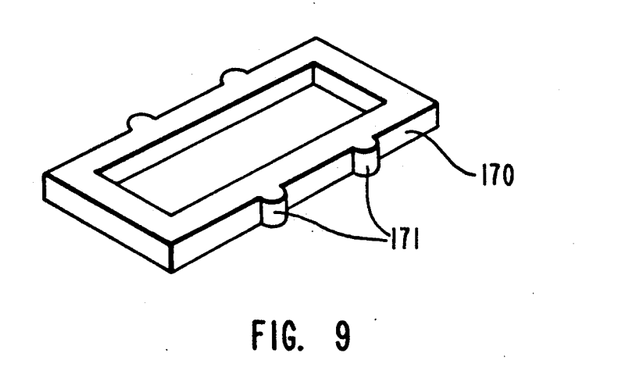

FIG. 9 illustrates a further alternative embodiment wherein projections 171 on the side portions 170 serve as lateral restraints for the ligament. The projections may have a configuration of pillars or other convenient shapes.

Figure 10:
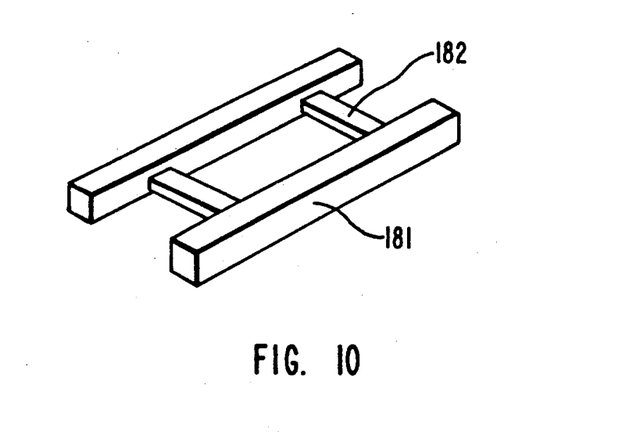

FIG. 10 illustrates a stirrup wherein the cross members 182 are recessed relative to the side portions 181 so that the staple (not shown) does not protrude far above the stirrup as in the previous embodiments of the invention, when driven into the bone.

Figure 11:
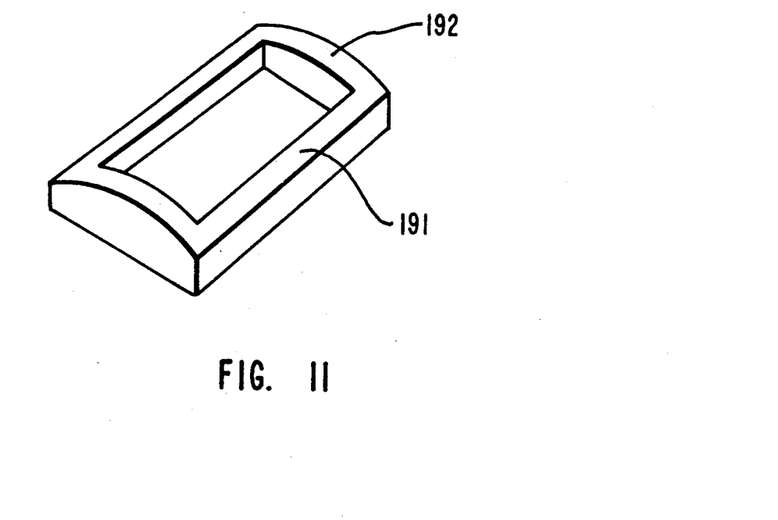

In FIG. 11 the side portions 192 are rounded from the centre to the side portions 191, reducing the profile of the assembled staple.

Figure 12:
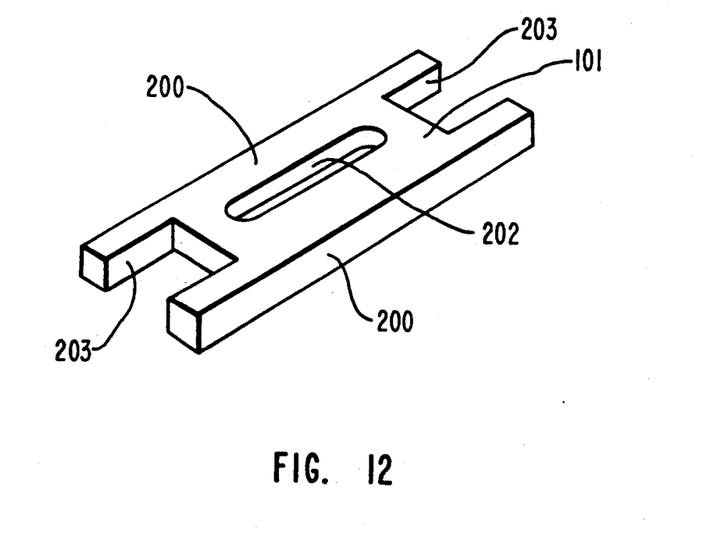

FIG. 12 illustrates a stirrup having side portions 200 and wherein the lateral dimension of the aperture 202 is less than that of the staple receiving apertures 203, enhancing the rigidity of the stirrup.

Features of the stirrup shown in FIGS. 3 to 12 may be interchanged or combined as desired. For example the stirrup shown in FIG. 3 may incorporate chamfered surfaces as shown in FIGS. 6 and 7.

As described earlier, FIG. 1 shows a stirrup 101 engaged upon the legs 106 of a staple 101. The stirrup is allowed to slide freely along the legs of the staple prior to implantation. FIG. 2 illustrates installation of the staple shown in FIG. 1 in which ligament 103 is engaged upon the stirrup 102 by threading through the aperture 110 followed by a rotation of the stirrup 102 through 180°. This wraps the ligament and the stirrup as shown in FIG. 2. The staple is then inserted through the apertures in the stirrup as shown and then driven home into bone 104 in order to secure the ligament.

Figure 13:
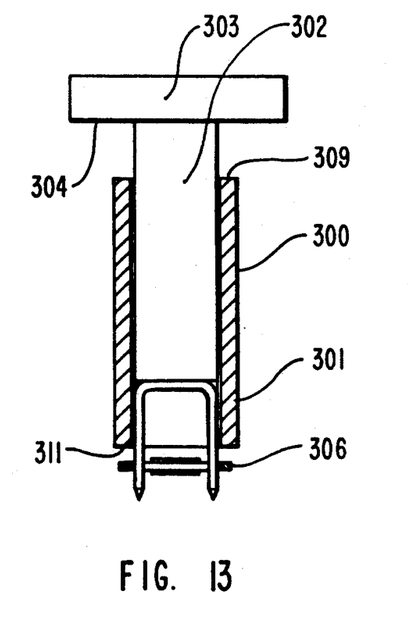
Figure 14:
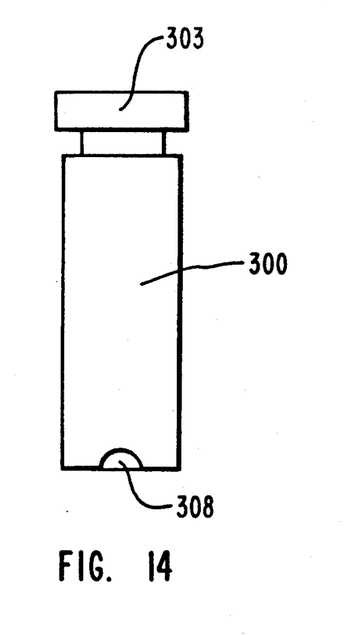
Figure 15:
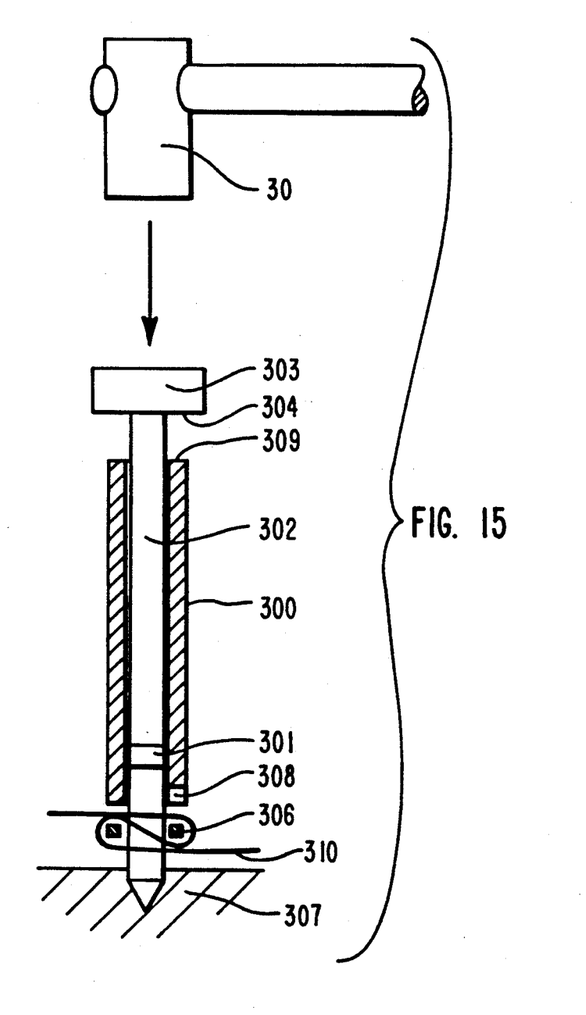

FIGS. 13 to 15 illustrate a tool for use in implantation of bone staples, particularly but not exclusively staples in accordance with the present invention.

A sleeve 300 defining a tubular guideway is dimensioned to allow reception of the head of the staple 301, so that the staple can slide within the sleeve but is constrained from twisting or other lateral motion. The sleeve may incorporate a hand grip (not shown) or other means to facilitate correct orientation during installation.

A driver 302 having a striking plate 303 is arranged to slide within the sleeve when the striking plate is struck with a hammer 305, abutting the head of a staple 301 to drive the latter into the bone. The driver is held captive within the sleeve, for example by means of a peg located in a channel in the sleeve, preventing complete withdrawal of the driver from the sleeve. Abuttment of the lower surface 304 of the striking plate against the top 309 of the sleeve 300 is arranged to allow the staple to be driven into a bone 307 to the correct depth, the length of the driver 302 being shorter than that of the sleeve 300 by a distance selected to allow the head of the staple 301 to protrude from the bone, allowing the stirrup 306 and ligament 310 to be tightly held but not impacted into the bone. Abuttment of the lower end 311 of the sleeve with the stirrup 306 and ligament 310 holds the latter securely while the staple is being driven home. An aperture 308 in the side of the sleeve allows observation of the head of the staple as the latter is driven home.

Woven ligaments disclosed in EP 0126520 may be used in conjunction with staples of the present invention. Sheathed ligaments as described in U.S. Pat. No. 4,775,380 are preferred. In preferred embodiments of the invention the ligaments disclosed in the prior specification are modified with elongate densely woven portions at the head and or tail thereof to facilitate threading of them through the stirrup-staple assembly during installation. The ends of the densely woven portions may be pointed, tapered or otherwise narrowly formed to facilitate threading through the stirrup-staple assembly.

Figure 16:
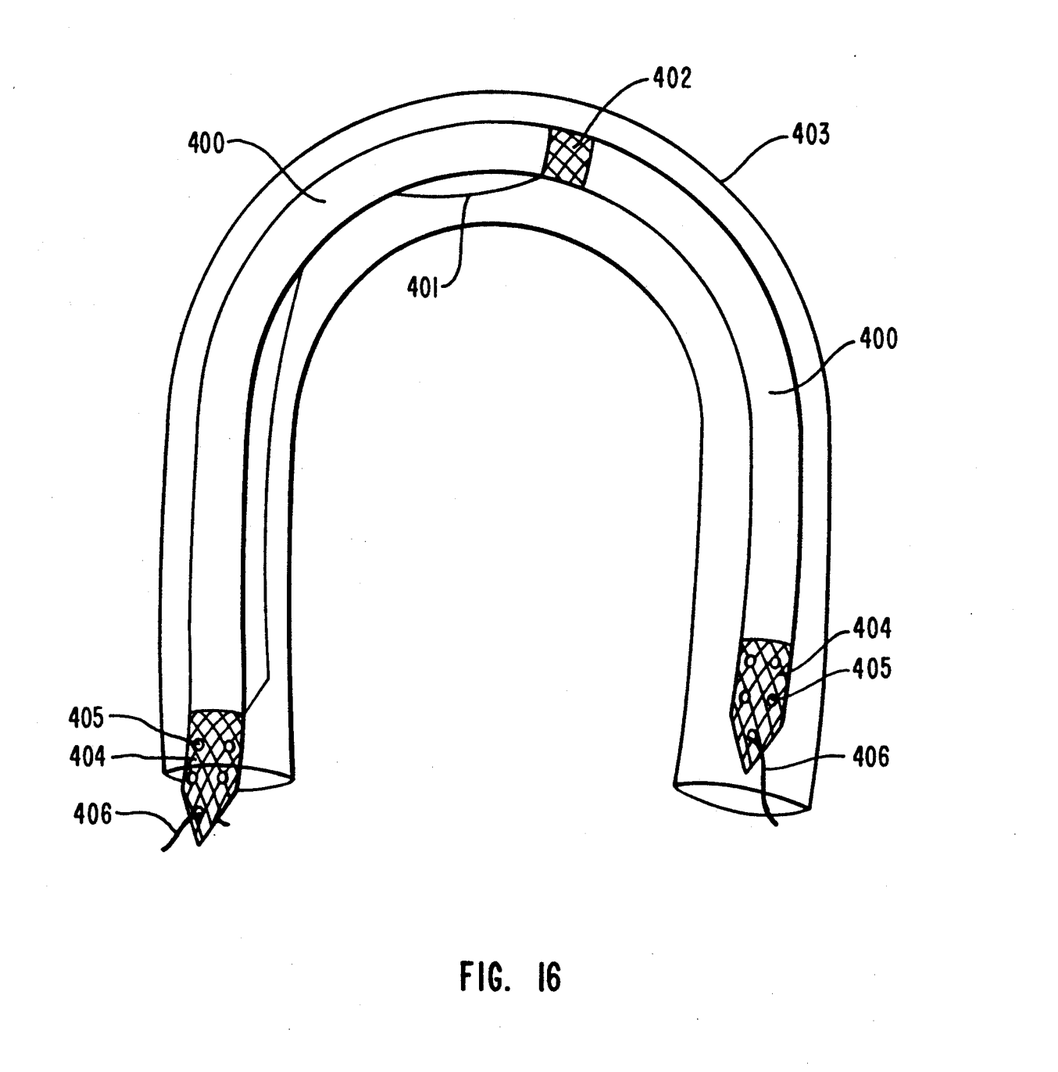
FIG. 16 illustrates in more detail one example of a ligament for use with a fixation device according to the invention.

FIG. 16 shows a woven ligament comprising tubular portion 400, a side opening pouch 401 for receiving a bone plug and densely woven portion 402 adjacent the pouch. The ligament is disposed within a tubular plastics sheath 403 to facilitate insertion through a bone during implantation. Ends of the ligament are formed into densely woven portions 404 which are tapered at the ends to facilitate threading through the staple during implantation. The densely woven portions 404 each have a plurality of holes 405 though which threads 406 may pass or which may be engaged by tools during implantation.

Use of a fixation device in accordance with this invention confers many advantages. The staple has a simple construction and is not weakened by the need to provide grooves for engagement with a tool. The staple driving tool has a simple construction and may be engaged with the head of a staple without requiring use of both hands. The tool serves to hold the staple perpendicular to the bone during installation. The tools allow quick and stable holding of the staple, without the need for fastening means such as screws. The direction of actions during the use of the tool is downward, thus keeping the staple secure within the buckle plate and pressed against the bone. Other tools require action in directions that may dislodge the staple from the buckle plate and so requiring the process of assembling the fixation to be repeated. Moreover the tool may be simply removed from the staple after implantation of the latter, without need for unfastening of any clamping arrangement. Unfastening of a clamping arrangement may disturb and loosen the staple.

We claim:

1. A ligament fixation device for securing a ligament to a bone and which comprises a bone staple having a head portion by which the staple can be driven into the bone, and a pair of legs extending away from the head portion and having ends engageable into the bone, characterized by a stirrup for guiding the driving movement of the staple and co-operable with the staple in order to anchor the ligament to the bone, characterized in that the stirrup has guides to engage the legs of the staple and thereby guide the driving movement of the staple, and an aperture formed in the stirrup and defined between a pair of opposed side edges, said aperture permitting the ligament to be received by the stirrup in serpentine manner with a first portion to be located between the stirrup and the bone, a second portion to pass around one of said side edges of the aperture, through the aperture and around the other side edge, and a third portion to be located between the head portion of the staple and the stirrup, whereby to anchor the ligament to the bone when the staple is driven into the bone.

2. A device as defined in claim 1 in which the stirrup comprises side portions and at least two cross-members extending between side portions of the stirrup at positions intermediate the ends of the side portions in order to define said aperture, and also to define said guides through which the staple legs can be received.

3. A device as defined in claim 1, in which the stirrup is symmetrical in construction.

4. A device as defined in claim 1, in which the stirrup includes chamfered or otherwise profiled edges to minimize wear of the ligament.

5. A device as defined in claim 1, comprising spikes provided on the underside of the stirrup to secure the latter to ligament or adjacent bone.

6. A device as defined in claim 1, in which the side portions of the stirrup are provided with recessed portions to hold the ligament captive against lateral movement.

7. A device as defined in claim 1, in which the cross-members which interconnect the side portions of the stirrup are of smaller thickness than the side portions to enable the head portion of the staple to be located substantially within the stirrup upon completion of driving of the staple into the bone.

8. A device as defined in claim 1, in which the stirrup is rectangular in shape, having side portions and cross-member end portions which define an aperture in which the staple can be received, the ligament also being capable of being taken through this aperture and of being securely anchored therein when the head of the staple is driven to a position in which it is located within the aperture.

9. A device as defined in claim 1, in which the stirrup comprises side portions and at least two intermediate cross-members which interconnect said side portions in order to define end apertures through which the staple legs can be taken.

10. A device as defined in claim 1, and in combination with a prosthetic ligament to form a ligament fixation system, in which the prosthetic ligament has tapered ends to facilitate threading of the ligament through the aperture in the stirrup.

11. A device as defined in claim 10, in which the tapered ends are densely woven sections.

12. A device as defined in claim 11, in which a removable protective sheath surrounds the ligament.

13. A device as defined in claim 10, in which the ligament includes a pouch and a bone plug, and a densely woven section adjacent to the bone plug.

14. A fixation device for securing a ligament to a bone and which comprises a bone staple having a head portion by which the staple can be driven into the bone, and a pair of legs extending from the head portion and having ends engageable into the bone, characterized by a stirrup, for guiding the driving movement of the staple, co-operable with the staple in order to anchor the ligament to the bone, said stirrup having guides to receive the legs of the staple and to guide the driving movement of the legs, and also having an aperture through which the ligament can be taken prior to securement of the ligament to the bone, and further characterized by at least two cross-members which interconnect side portions of the stirrup and which are disposed outwardly of the guide postions through which the staple legs are received.

15. A fixation device for securing a ligament to a bone and which comprises a bone staple having a head portion by which the staple can be driven into the bone, and a pair of legs extending from the head portion and having ends engageable into the bone, characterized by a stirrup, for guiding the driving movement of the staple, co-operable with the staple in order to anchor the ligament the bone, said stirrup having guides to receive the legs of the staple and to guide the driving movement of the legs, and also having an aperture through which the ligament can be taken prior to securement of the ligament to the bone, and further comprising cross-members which interconnect the side portions of the stirrup which are of smaller thickness than the side portions to enable the head portion of the staple to be located substantially within the stirrup upon completion of driving of the staple into the bone.

16. A fixation device for securing a ligament to a bone and which comprises a bone staple having a head portion by which the staple can be driven into the bone, and a pair of legs extending from the head portion and having ends engageable into the bone, characterized by a stirrup, for guiding the driving movement of the staple, co-operable with the staple in order to anchor the ligament to the bone, said stirrup having guides to receive the legs of the staple and to guide the driving movement of the legs, and also having an aperture through which the ligament can be taken prior to securement of the ligament to the bone, and wherein the stirrup is rectangular in shape, having side portions and cross-member portions which define an aperture in which the staple can be received, the ligament also being capable of being taken through this aperture and of being securely anchored therein when the head of the staple is driven to a position in which it is located within the aperture.

17. A fixation system having a fixation device for securing a ligament to a bone and which comprises a bone staple having a head portion by which the staple can be driven into the bone, and a pair of legs extending from the head portion and having ends engageable into the bone, characterized by a stirrup, for guiding the driving movement of the staple co-operable with the staple in order to anchor the ligament to the bone, said stirrup having guides to receive the legs of the staple and to guide the driving movement of the legs, and also having an aperture through which the ligament can be taken prior to securement of the ligament to the bone, and including a prosthetic ligament to be taken through the aperture in the stirrup, the prosthetic ligament having tapered ends to facilitate the threading of the ligament through the aperture in the stirrup, and wherein the ligament further includes a pouch and a bone plug, and a densely woven section adjacent to the bone plug.

* * * * *

UNITED STATES PATENT AND TRADEMARK OFFICE
CERTIFICATE OF CORRECTION

PATENT NO. : 5,209,756
DATED : May 11, 1993
INVENTOR(S) : BAHAA B. SEEDHOM et al.

It is certified that error appears in the above-identified patent and that said Letters Patent is hereby corrected as shown below:

Column 2, line 4, "minimise" should be --minimize--
Column 2, line 66, after "fixation" insert --a--
Column 3, line 60, "minimise" should be --minimize--
Column 4, line 10, "centre" should be --center--
Column 6, line 62, after "ligament" insert --to--

Signed and Sealed this

Eighth Day of March, 1994

Attest:

BRUCE LEHMAN

Attesting Officer

Commissioner of Patents and Trademarks